(12) United States Patent
Qin et al.

(10) Patent No.: US 7,663,026 B2
(45) Date of Patent: Feb. 16, 2010

(54) TRANSFORMATION OF SEAWEED UTILIZING BIOLISTIC GENE TRANSFER TO SPORES

(75) Inventors: Song Qin, Shandong (CN); Peng Jiang, Shandong (CN); Daozhan Yu, Shandong (CN); Fuchao Li, Shandong (CN); Guoqiong Sun, Shandong (CN)

(73) Assignee: Institute of Oceanology Chinese Academy of Sciences, Shandong (CN)

( * ) Notice: Subject to any disclaimer, the term of this patent is extended or adjusted under 35 U.S.C. 154(b) by 544 days.

(21) Appl. No.: 10/546,558

(22) PCT Filed: Jul. 7, 2003

(86) PCT No.: PCT/CN03/00534

§ 371 (c)(1), (2), (4) Date: Aug. 23, 2005

(87) PCT Pub. No.: WO2004/076671

PCT Pub. Date: Sep. 10, 2004

(65) Prior Publication Data

US 2006/0154355 A1  Jul. 13, 2006

(30) Foreign Application Priority Data

Feb. 26, 2003  (CN) ................................ 03 1 11061

(51) Int. Cl.
*C12N 15/82* (2006.01)

(52) U.S. Cl. ...................... 800/293; 800/288; 800/292; 800/296; 435/468

(58) Field of Classification Search ...................... None
See application file for complete search history.

(56) References Cited

FOREIGN PATENT DOCUMENTS

CN         1157326         8/1992

OTHER PUBLICATIONS

Song et al. A transformation model for *Laminaria japonica* (Phaeophyta, Laminariales). (1998) Chin. J. Oceanol. Limnol.; vol. 16, Suppl.; pp. 50-55.*
Jiang, et al., "Expression of Hepatitis B Surface Antigen Gene (HBsAg) in *Laminaria japonica* (Laminariales, Phaeophyta)," Chin. Sci. Bullet. 2002, 47(17): 1095-1097. (English Abstract Only).
Yu et al., "Transient Expression of lacZ Reporter Gene In the Economic Seaweed *Undaria pinnatifida*," High Technol. Letters 2002, 12(8):93-95. (English Abstract Only).

* cited by examiner

*Primary Examiner*—Cathy Kingdon Worley
(74) *Attorney, Agent, or Firm*—Smith, Gambrell & Russell, LLP

(57) ABSTRACT

This invention relates to marine algae, and more particularly, to a method for producing improved seaweed strains by genetic engineering. The vector for transformation were constructed by inserting the high-plant or algae-derived promoters upstream of foreign reporter genes or such cassettes that functional genes are fused with antibiotics or herbicide-resistant genes. The genetic seaweed was generated by natural development process by recombinated plasmid DNA introduction to seaweed spore with Biolostics as transformation methods. Introduced traits of antibiotics or herbicide-resistance were used to select the transgenic seaweed individuals when foreign functional genes are transformed. Stable transformation could be obtained following this invention.

10 Claims, No Drawings

US 7,663,026 B2

TRANSFORMATION OF SEAWEED UTILIZING BIOLISTIC GENE TRANSFER TO SPORES

FIELD OF THE INVENTION

This invention relates to marine algae, and more particularly, to the method for producing improved seaweed strains by genetic engineering.

BACKGROUND OF THE INVENTION

Phycocolloids are natural gums produced by and extracted from marine algae. The three principal types of commercially valuable phycocolloids are agar, carrageenan and alginate. By far the seaweeds which have been successfully cultivated include red algae (*Porphyra, Gracilaria, Gelidium, Euchema*), green algae (*Ulva*) and brown algae (*Laminaria, Undaria*). The global cultivation areas for seaweeds are 3 million mu, with annual production more than 6.35 million tons (wet weight), most of which were utilized to extract the phycocolloids, except a small amount as nutrition food. In recent years, due to quickly-increased demands to the phycocolloids production and quality improvement, the genetic transformation techniques were introduced to the seaweed research fields, with purpose to directionally improve the seaweeds traits, also the great potential for expression of high-value products has been suggested.

To date, most of the well-developed techniques to generate transgenic plant are employed for high plants, which include: 1. Transformation methods: *Agrobactarium* Ti plasmid-mediated transformation, electroporation to protoplast, and Biolistics to explant; 2. Vector element: high plant-derived promoters (i.e. CaMV35S) have been used widely to drive the expression of foreign genes; 3. Transformation recipient and plant regeneration: to take advantage of the totipotency, that is to regenerate protoplast, or induce the callus formation and further differentiation to regenerate new plant; 4. Selectable marker: Npt II gene was used most widely as selectable marker that, transgenic plant could be obtained by selection with kanamycin or neomycin.

Seaweeds are low plants that live in marine environment, they are of significant difference which including: 1. Transformation methods: no well-developed methods like *Agrobactarium* Ti plasmid-mediated transformation to high plant; 2. Vector element: no seaweed-derived promoter has been obtained; 3. Transformation recipient and plant regeneration: there's significant difference on research extent between species, protoplast regeneration was easy in some genus like *Porphyra,* but very hard in others like *Laminaria* and *Undaria,* as well as low efficiency for callus induction; 4. Selectable marker: sensitive antibiotics types and sensitivity extent maybe different between seaweed and high plant.

By far most researches on seaweed transformation have referred the techniques applied in high plant, those are to transfer the seaweed explants or protoplast as transformation recipient. Only transient expression has been obtained, and no expression was detected in regenerated plant, even the transient transformation efficiency is low since only high plant-derived promoters (e.g. CaMV35S) are available; no sensitivity test on seaweed to antibiotics have been done yet.

SUMMARY OF THE INVENTION

Aiming to solve such difficulties referenced above, this invention provides the method for producing improved seaweed strains by genetic engineering with high efficiency and stable expression, taking advantage of seaweed life cycle characters.

In order to realize the purposes above-mentioned, the technical program of this invention is as follows. The vector for transformation were constructed by inserting the high-plant or algae-derived promoters upstream of foreign reporter genes or such cassettes that functional genes fused with antibiotics or herbicide-resistant genes. The seaweed spore was employed as transformation recipient and bombed with recombinated plasmid DNA by Biolistics, thus the genetic seaweed could be generated by natural development process. Introduced traits of antibiotics or herbicide-resistance were adopted to select the transgenic seaweed individuals when foreign functional genes are transformed, therefore, to obtain further the foreign gene products (e.g. expressed vaccine, defensin, antibody, medical protein).

Wherein the said foreign functional genes are those encoding phycobillisome, growth factor, antibody, vaccine, defensin or antibacterial peptide and so on; said antibiotics or herbicide-resistant genes are cat, hpt or bar; said antibiotics are chloramphenicol or hygromycin; said herbicide is Basta; said promoters are SV40 promoter, CaMV35S promoter, ubiquitin promoter or algae-derived fcp promoter and so on; said selectable marker-selectable reagent cassettes are cat-chloramphenicol, hpt-hygromycin or bar-Basta.

Compared with present techniques employed in seaweeds, this invention is an entire innovation which addressed significant improvement as bellows:

1. In terms of transformation methods, although Biolistics is a universal penetrating-cell wall method with a wide range of available target cell, this invention is the first one to offer the seaweed spores as transformation recipient in the field.

2. In terms of vector element, the experiments of this invention shown that available promoters for seaweed has been explored a lot among those derived from both high plant and algae.

3. In terms of transformation recipient, the second original creation of this invention is to obtain non-chimeric expression of transgenic plant by using seaweed spore as transformation recipient. For most cultivated seaweed, pure germ plasm bank have been set up by using their microscopic life stage, such as male and female gametophytes in *Laminaria* and *Undaria,* filamentous sporophytes in *Prophyra,* and techniques to generate new plant from seaweed spore have been well developed, which contribute reliable materials for spore-mediated transformation in seaweed.

4. In terms of selectable marker, research results of this invention shown that *Laminaria* and *Undaria* are sensitive to chloramphenicol, much more to hygromycin, and most sensitive to Basta, thus three selectable marker-selectable reagent cassettes are applicable including cat-chloramphenicol, hpt-hygromycin and bar-Basta.

5. Stable expression of foreign gene could be obtained by this invention, in the case of lacZ reporter gene transformation to *Laminaria* male gametophytes, the transformation efficiency in zygote sporophytes is up to 50%, with expression efficiency up to 30%.

DESCRIPTION OF THE INVENTION IN DETAIL

The invention will be further described in detail with reference to drawings attached and examples below.

EXAMPLE 1

Invention Effective to *Laminaria* Female Gametophytes with Reporter Gene Transformation A vector contains GUS reporter gene driven by fcp promoter (from marine diotam-derived fcp gene encoding fucoxanthin-chlorophyll a/c binding protein) was introduced to *Laminaria* female gametophytes by Biolistics, resulting in stable expression of GUS gene in parthenogenetic sporophytes, detailed description is as below:

1. Preparation of Micro-Particle for Biolistics:

To weight 60 mg golden powder (accessory to Biolistics, BIO-RAD, USA, 1.0 μm in diameter) and add 1 ml ethanol, vortex for 1 min followed by brief centrifuge at 10000 rpm for 10 sec. To remove the supernatant, wash the golden particle by adding 1 ml autoclaved water to resuspend and centrifuging to remove the supernatant, repeat the wash process for 3 times, resuspend the golden particle in final 1 ml autoclaved water, aliquot into 50 μl each and store at 4° C.

Before transformation, each aliquot (50 μl) was transferred to a 1.5 ml centrifuge tube, and added into 5 μl DNA (1 μg/μl), 50 μl $CaCl_2$ (2.5 mol/L), 20 μl spermidine (0.1 mol/L) in order during continuous vortexing, last to vortex for 3 min, centrifuge at 10000 rpm for 10 sec and remove the supernatant, wash the pellet by using 250 μl ethanol for 2 times, resuspend the golden particle in 60 μl ethanol.

2. Transformation to *Laminaria* Female Gametophytes:

In 1-2 days before transformation, to gently grind the *Laminaria* female gametophytes by using 2 pieces of autoclaved glass slides, to separate the filamentous to a extent that no fragments more than 5 cells could be detected under microscope. To count the cells by a hematimeter and culture the suspension in dark overnight. Round autoclaved silk sieve cloth (400 mesh) was used as carrier for target cells, which are tiled as a round and thin layer with diameter in 2 cm in the middle of the cloth. Each sample containing $1.0 \times 10^6$ female gametophyte cells was transformed once with about 12 μl resuspension of golden particle.

Biolistics (Type: PDS1000/He) used for transformation is product of BIO-RAD Ltd. Company, USA. Both table-board and outside and inside surface of Biolistics was sterilized with 70% ethanol, involved accessories including Rupture Disk, DNA Macrocarrier and Stopping Screen which are all rinsed in 70% ethanol for 20 min, and dried under UV light. Biolistics parameters used for transformation are: the distance between target cells and Stopping Screen is 6.0 cm, vacuum is 28 (inch mercury column).

Control groups which were transformed with empty golden particle, i.e. no DNA coated, were also set up, sharing the same procedure.

3. Culture After Transformation:

After transformation, *Laminaria* female gametophytes from both treatment and control group were transferred to Ferric-containing sea water media (prepared by using autoclaved sea water, containing $NaNO_3$ 0.71 mmol/L, $KH_2PO_4$ 0.032 mmol/L, Ferric citric 0.0019 mmol/L, $V_{B12}$ 0.5 μg/L), at temperature 10.0±0.5° C., under light cycle of L:D=10 h/14 h, and the illumination degree of 100 μmol·$m^{-2}·s^{-1}$. The same media was employed for parthenogenetic juveniles under the same condition, with media renewed every week.

4. Detection for Integration and Expression of GUS Gene:

The in situ histo-chemical staining method was adopted to detect the GUS expression in parthenogenetic sporophytes of *Laminaria*. Positive result was obtained by PCR, suggesting the occurrence of integration of GUS gene. Whereas no expression was detected in control group transformed with empty golden particle without DNA coated.

In this description, foreign genes refer to those exogenous to the target seaweed, including both reporter gene helpful to set up the transformation model, and functional gene encoding certain protein or peptides with applicable utilization, such as vaccine, antibody and so on. In this example, the foreign gene is a kind of reporter gene. The promoter refers to a special nuclear acids sequence, which can drive the expression of foreign gene.

EXAMPLE 2

Invention Effective to Both Female and Male *Laminaria* Gametophytes with Reporter Gene Transformation. (the Example 1 and 2 are Methodology Proof for Spore-Mediated Transformation)

A vector contains lacZ reporter gene driven by SV40 promoter was introduced to both female and male *Laminaria* gametophytes by Biolistics, resulting in stable expression of lacZ gene in zygotic sporophytes. All procedures about golden particles preparation and Biolistics transformation are as same as in Example 1. Procedures for target cells preparation are same between female and male gametophytes. Subsequent steps are:

3. Culture After Transformation:

After transformation, *Laminaria* gametophytes from both treatment and control group were transferred to Ferric-containing sea water media as in example 1 under the same culture condition. To add the same amount of non-transformed male gametophytes to female transformed gametophytes and non-transformed female gametophytes to male transformed gametophytes respectively. Same media was employed for zygotic sporophytes juveniles under the same condition, with media renewed every week.

4. Detection for Integration and Expression of lacZ Gene:

in situ histo-chemical staining method was employed to detect the lacZ expression in zygotic sporophytes of *Laminaria*, positive result was obtained in both male gametophytes-mediated and female gametophytes-mediated treatment groups. Transformation efficiency in the former is 50%, expression efficiency (calculated as percentage of stained area in whole area of each positive individual) is about 30%, showing a significant enhancement compared with the latter (as Transformation efficiency 20% and expression efficiency 4-5%). There is 1.9% of individuals in former group showed uniform expression, combined with the positive PCR results, it has suggested that the integration of lacZ gene occurred at one-cell stage.

EXAMPLE 3

Extension to Utilization, Both Functional Foreign Gene and Selectable Marker were Used A vector contains a cassette (selectable marker cat-vaccine gene HBsAg encoding Hepatitis B surface antigen) driven by SV40 promoter was introduced to *Laminaria* male gametophytes by Biolistics, resulting in stable expression of HBsAg gene in zygotic sporophytes after chloramphenicol selection.

All the procedures about golden particles preparation, male gametophytes cells preparation and Biolistics transformation are as the same as in the Example 1. The procedures for culture after transformation are as the same as in the Example 2. Subsequent steps are:

3. Selection by Chloramphenicol

Chloramphenicol selection was performed in autoclaved beakers by adding N-P-containing sea water media, chloramphenicol and zygotic sporophytes juveniles reaching 2 cm in length. Chloramphenicol concentration was 20 μg/ml during the first 2 days, and increased to 50 μg/ml during the 3th-7th day, with media renewed everyday.

4. Detection to Integration and Exression of HBsAg Gene

The HBsAg expression in 38 samples was determined by quantified ELISA method, and 13 samples (34.21%) were positive, determined expression level is up to 1.2 μg/(mg soluble protein), averaging 0.465 μg/(mg soluble protein). The positive PCR result suggests the successful integration of HBsAg gene.

5. Application of Transgenic Kelp Expressing HBsAg

Some research has showed that there's no significant difference on vaccine dosage between vessel injection and oral administration. Injection dosage for an adult is about 15 μg, corresponding to about the same amount of vaccine expressed in 2.5 g (fresh weight) of transgenic kelp, suggesting a great application potential for transgenic seaweed by using this invention.

Selectable marker refers to a antibiotics or herbicide resistance gene, whose expression will benefit the host cell to survive under the corresponding antibiotics or herbicide pressure, whereas others without this selectable marker will die. In this example, the functional foreign gene is vaccine HBsAg gene, and the selectable marker is cat gene.

EXAMPLE 4

Extension to Utilization, Both Functional Foreign Gene and Selectable Marker were Used A vector contains a cassette (selectable marker hpt-defensin gene) driven by SV40 promoter was introduced to *Laminaria* female gametophytes by Biolistics. The positive PCR result was obtained in survivals of parthenogenetic sporophytes after hygromycin selection.

All procedures about golden particles preparation, female gametophytes cells preparation and Biolistics transformation are as the same as in the Example 1. Hygromycin selection was performed in autoclaved beakers by adding N-P-containing sea water media, hygromycin and zygotic sporophytes juveniles reaching 1-2 cm in length. Hygromycin concentration was 50 μg/ml, with media renewed every week.

EXAMPLE 5

Invention Effective to *Undaria* with Reporter Gene Transformation

A vector contains lacZ reporter gene driven by SV40 promoter was introduced to *Undaria* male gametophytes by Biolistics, resulting in stable expression of lacZ gene in both male gametophytes and zygotic sporophytes.

All procedures about golden particles preparation, male gametophytes cell preparation and Biolistics transformation are as the same as in the Example 1. The pocedures for culture after transformation are as the same as in the Example. Subsequent steps are: in situ histo-chemical staining method was used to detect the lacZ expression. The positive result was obtained in both male gametophytes and zygotic sporophytes.

Transformation efficiency in the latter is to 70%, the integration of lacZ gene was suggested by positive PCR results.

The said functional foreign genes in this invention also include those encoding phycobillisome, growth factor, antibody or antigen; Said antibiotics or herbicide resistance genes also include bar gene; Said herbicide also include Basta; Said promoters also include CaMV35S promoter or ubiquitin promoter; Said selectable marker-selectable reagent combinations also include bar-Basta; Said reporter gene also include luc gene or GFP gene.

What is claimed:

1. A method to establish a transgenic seaweed, comprising the following steps:
    constructing a vector by inserting a high-plant or algae-derived promoter upstream of a foreign reporter, a functional nucleic acid or a nucleic acid molecule which confers resistance to an antibiotic or a herbicide;
    introducing the vector into a male gametophyte of *Laminaria* using electroporation or a biolistic transformation method;
    generating the transgenic seaweed through a natural development process.

2. The method to establish a transgenic seaweed according to claim 1, and further comprising using the antibiotic or the herbicide to select the transgenic seaweed.

3. The method to establish a transgenic seaweed according to claim 1 or 2, wherein said functional nucleic acid encodes phycobillisome, a growth factor, an antibody, a vaccine, a denfensin, or an antibacterial peptide.

4. The method to establish the transgenic seaweed according to claim 1 or 2, wherein said promoter is a SV40 promoter, a CaMV35S promoter, a ubiquitin promoter, or an algae-derived fcp promoter.

5. The method to establish the transgenic seaweed according to claim 1 or 2, wherein said nucleic acid molecule is a cat gene, a hpt gene, or a bar gene.

6. The method to establish the transgenic seaweed according to claim 1 or 2, wherein the antibiotic is chloramphenicol or hygromycin.

7. The method to establish the transgenic seaweed according to claim 1 or 2, wherein said herbicide is Basta.

8. The method to establish the transgenic seaweed according to claim 1 or 2, wherein said transformation method is a biolistic transformation method.

9. The method to establish the transgenic seaweed according to claim 1 or 2, wherein the nucleic acid molecule is a cat gene and the antibiotic is chloramphenicol, the nucleic acid molecule is a hpt gene and the antibiotic is hygromycin, or the nucleic acid molecule is a bar gene and the herbicide is Basta.

10. The method to establish a transgenic seaweed according to claim 1, wherein said foreign reporter includes a GUS gene, a lacZ gene, a luc gene, or a GFP gene.

* * * * *